US008696540B2

United States Patent
Mehta et al.

(10) Patent No.: US 8,696,540 B2
(45) Date of Patent: Apr. 15, 2014

(54) APPARATUS AND METHOD TO SHIELD RADIATION NEEDLES

(75) Inventors: Rohit Mehta, Clifton, VA (US); Rashmi Amin, Springfield, VA (US)

(73) Assignee: Best Medical International, Inc., Springfield, VA (US)

( * ) Notice: Subject to any disclaimer, the term of this patent is extended or adjusted under 35 U.S.C. 154(b) by 187 days.

(21) Appl. No.: 13/052,593

(22) Filed: Apr. 5, 2011

(65) Prior Publication Data

US 2012/0277519 A1 Nov. 1, 2012

(51) Int. Cl.
*A61G 5/00* (2006.01)
*G21F 5/015* (2006.01)
*G21F 5/018* (2006.01)
*G21F 5/12* (2006.01)

(52) U.S. Cl.
USPC .......................... 600/8; 250/506.1; 250/507.1

(58) Field of Classification Search
USPC ....................................... 600/7, 8; 250/507.1
See application file for complete search history.

(56) References Cited

U.S. PATENT DOCUMENTS

| 5,460,592 | A  | * | 10/1995 | Langton et al. | ............ 600/7 |
| 6,472,675 | B2 | * | 10/2002 | White et al. | ........... 250/506.1 |
| 6,619,476 | B2 | * | 9/2003 | Hoch et al. | .............. 206/380 |
| 2009/0057580 | A1 | * | 3/2009 | Wissman et al. | ....... 250/506.1 |
| 2011/0118532 | A1 | * | 5/2011 | Kaplan | ...................... 600/8 |

* cited by examiner

*Primary Examiner* — Charles A Marmor, II
*Assistant Examiner* — Thaddeus Cox

(57) ABSTRACT

According to one general aspect there is a needle package apparatus that comprises a top portion and a bottom portion; a plurality of needle slots exact distance apart that allows to place a plurality of needles that contain radioactive seeds; a cylindrical coil that is inserted to the plurality of needle slots to hold said plurality of needles, wherein said cylindrical coil prevents the leakage of the radiation from the radioactive seeds; a set of hinges located at the end of said needle package within the outer most said plurality of needle slots; wherein the hinges can be bend to change the angle of said top portion of said needle package by a medical personnel to create a stand; and a single end enclosure located at the distal end of said cylindrical coil to provide an enclosed cylinder.

4 Claims, 3 Drawing Sheets

APPARATUS AND METHOD TO SHIELD RADIATION NEEDLES

CROSS REFERENCE TO RELATED APPLICATION

N/A

FIELD OF THE INVENTION

The invention generally relates to apparatus and method to shield radiation needles used the brachytherapy services.

BACKGROUND

Brachytherapy (from the Greek word brachys, meaning "short-distance"), also known as internal radiotherapy, scaled source radiotherapy, curietherapy or endocurietherapy, is a form of radiotherapy in which a radiation source is placed inside or next to the area requiring treatment. Brachytherapy is commonly used as an effective treatment for cervical, prostate, breast, and skin cancer and can also be used to treat tumors in many other body sites.

As the radiation sources can be precisely positioned at the tumor treatment site, brachytherapy enables a high dose of radiation to be applied to a small area. Furthermore, because the radiation sources are placed in or next to the target tumor, the sources maintain their position in relation to the tumor when the patient moves or if there is any movement of the tumor within the body. Therefore, the radiation sources remain accurately targeted. This enables clinicians to achieve a high level of dose conformity—i.e. ensuring the whole of the tumor receives an optimal level of radiation. It also reduces the risk of damage to healthy tissue, organs or structures around the tumor, thus enhancing the chance of cure and preservation of organ function.

The two main types of brachytherapy treatment in terms of the placement of the radioactive source are interstitial and contact. In the case of interstitial brachytherapy, the sources are placed directly in the target tissue of the affected site, such as the prostate or breast. Contact brachytherapy involves placement of the radiation source in a space next to the target tissue. This space may be a body cavity (intracavitary brachytherapy) such as the cervix, uterus or vagina; a body lumen (intraluminal brachytherapy) such as the trachea or esophagus; or externally (surface brachytherapy) such as the skin. A radiation source can also be placed in blood vessels (intravascular brachytherapy) for the treatment of coronary in-stent restenosis.

The dose rate of brachytherapy refers to the level or 'intensity' with which the radiation is delivered to the surrounding medium and is expressed in Grays per hour (Gy/h). Low-dose rate (LDR) brachytherapy involves implanting radiation sources that emit radiation at a rate of up to 2 Gy·hr-1. LDR brachytherapy is commonly used for cancers of the oral cavity, oropharynx, sarcomas and prostate cancer. Medium-dose rate (MDR) brachytherapy is characterized by a medium rate of dose delivery, ranging between 2 Gy·hr-1 to 12 Gy·hr-1. High-dose rate (HDR) brachytherapy is when the rate of dose delivery exceeds 12 Gy·hr-1. The most common applications of HDR brachytherapy are in tumors of the cervix, esophagus, lungs, breasts and prostate. Most HDR treatments are performed on an outpatient basis, but this is dependent on the treatment site.

Pulsed-dose rate (PDR) brachytherapy involves short pulses of radiation, typically once an hour, to simulate the overall rate and effectiveness of LDR treatment. Typical tumor sites treated by PDR brachytherapy are gynecological and head and neck cancers.

In order to accurately plan the brachytherapy procedure, a thorough clinical examination is performed to understand the characteristics of the tumor. In addition, a range of imaging modalities can be used to visualize the shape and size of the tumor and its relation to surrounding tissues and organs. These include x-ray radiography, ultrasound, computed axial tomography (CT or CAT) scans and magnetic resonance imaging (MRI). The data from many of these sources can be used to create a 3D visualization of the tumor and the surrounding tissues. Next, placement of the brachytherapy source applicators is determined by the clinical personnel. The source applicators are placed in the body and further imaged to ensure correct positioning of the applicators. Then, a 'virtual' patient and optimizing treatment plan is created. A 3D visualization is created of the patient and the applicators to refine the planned delivery of the radioactive sources. Last is the treatment delivery.

Prior to the treatment delivery, the radioactive seeds and needles must be ordered. The needles must be a custom gauge and the seeds come in different doses. The medical personnel must order the needle gauge and specifically determine the dose of each seed. Thereafter, the needles are inserted with the radiation seeds. The needles are then shipped to the medical personnel all over the country, when they are providing the treatment for the patient. The needles are shipped in big needle containers. The needle containers are covered with lead. This method of shielding increases the shipment cost to the patients and medical personnel. Furthermore, the problems that occur with the covering of the entire needles is radiation may leak, specifically, the covering of the needles may be removed or fall off of the needle package.

Therefore, one of ordinary skill in the art would appreciate that a method and apparatus be developed to reduce the shipment cost as well as provide a more effective way to enclose the radioactive seeds inside the surgical needles. In addition, a new method would be greatly appreciated to reduce the shipment cost as well to provide a more affordable health care treatment.

SUMMARY OF INVENTION

According to one general aspect there is a needle package apparatus that comprises a top portion and a bottom portion; a plurality of needle slots exact distance apart that allows to place a plurality of needles that contain radioactive seeds; a cylindrical coil that is inserted to the plurality of needle slots to hold said plurality of needles, wherein said cylindrical coil prevents the leakage of the radiation from the radioactive seeds; a set of hinges located at the end of said needle package within the outer most said plurality of needle slots; wherein the hinges can be bend to change the angle of said top portion of said needle package by a medical personnel to create a stand; and a single end enclosure located at the distal end of said cylindrical coil to provide an enclosed cylinder.

The needle package apparatus further comprises said cylindrical coil is composed of stainless steel, lead or Demron® wrap material, wherein the cylindrical coil diameter will not be greater than 6 mm.

The needle package apparatus further comprises said cylindrical coil is composed of a thickness of 1 mm to 3 mm, wherein the thickness depends on upon the activity of the radioactive seed.

The needle package apparatus further comprising said cylindrical coil is fixed within said plurality of needle slots and covers the entire needle with the radioactive seeds.

DETAILED DESCRIPTION

The following detailed description is provided to assist the reader in gaining a comprehensive understanding of the methods, apparatuses and/or systems described herein. Accordingly, various changes, modifications, and equivalents of the systems, apparatuses, and/or methods described herein will likely suggest themselves to those of ordinary skill in the art. Also, descriptions of well-known functions and constructions are omitted to increase clarity and conciseness.

The invention generally relates an apparatus and method to ship radioactive seeds.

Figure 1:
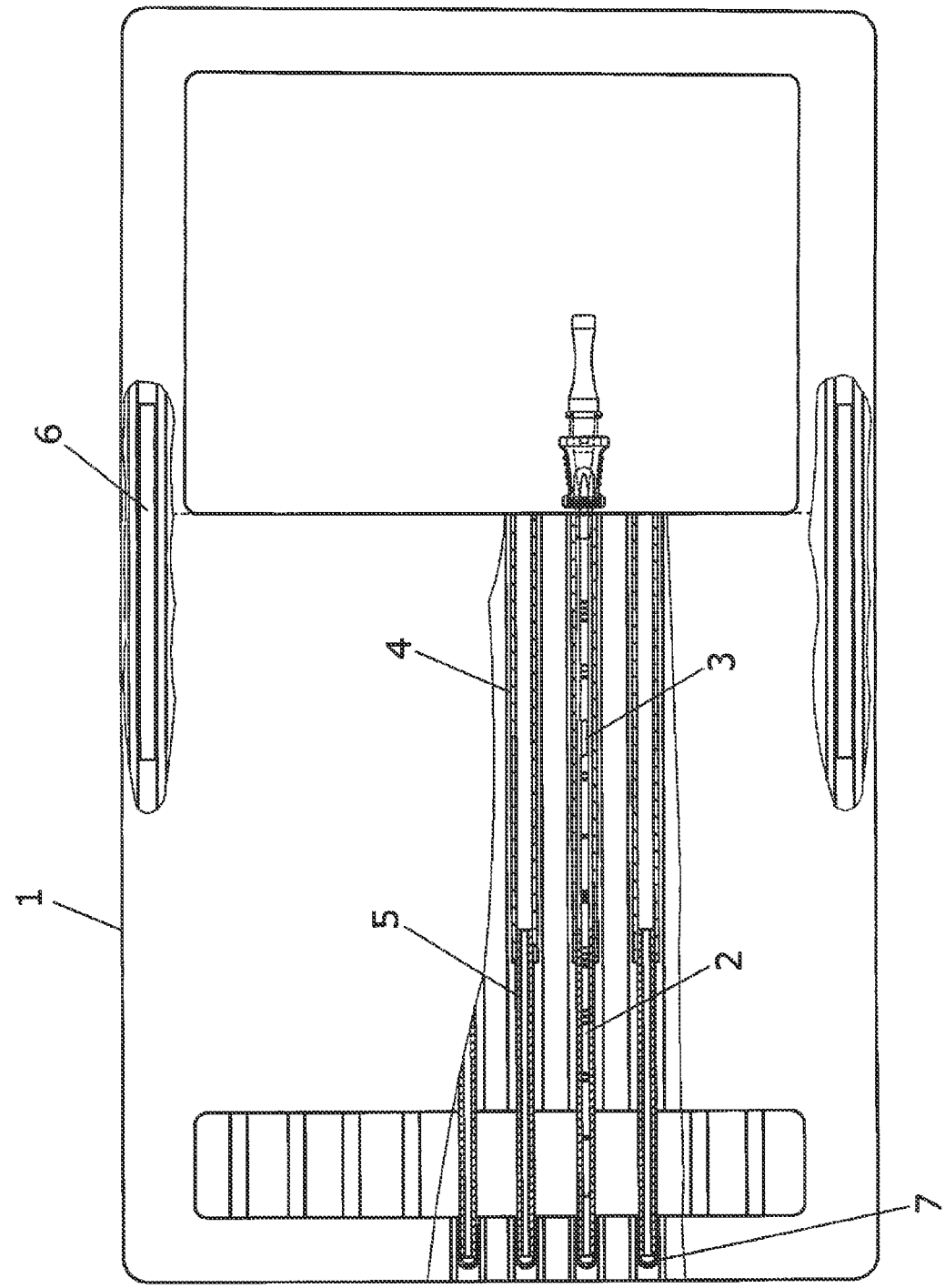
FIG. 1 is a diagram illustrating the top view of the radioactive needle holder.

FIG. 1. shows an exemplary layout of the shipment package. A needle package 1 contains, only for exemplary purposes, a single needle. The needle package 1 is custom for each order and depends on the number of needles required by the medical personnel for the treatment of the patient. The needle package contains sleeves. The sleeves will be spaced apart to provide add comfort and providing a small distance between each needle to allow medical personnel to remove the needle with case. For exemplary purposes, needle 2 is placed a needle case. The needle 2 contains a single radioactive seed 3. The radioactive seed can be placed anywhere inside the needle. For exemplary purposes, the needle 2 contains the radioactive seed 3 in the middle of the needle. Looking carefully, the radioactive need is inserted into the packaging case. The needle package 1 contains a circular tube 5 that is covered by an outer plastic tube 4. The circular tube 5 can be made of materials of stainless steel, lead based material or any material that can block the radiation from the radioactive seeds. The circular lead tube and circular outer plastic tube 4 are inserted into a single cut sleeve within in the needle package 2. This form of layering the outer plastic tube 4 with circular lead tube creates a solid fit, which cannot slide back and forth. Depending on the radiation level of the radioactive seed the thickness of the circular lead tube can be increased in size. This would provide more shielding and reduce the radiation leakage. At the bottom of the tubing is an end enclosure 7. The end enclosure prevents radioactive leakage from the bottom of the needle package 1. Each tube contains end enclosure 7 as well as a needle 2 with a radioactive source 3.

Figure 2:
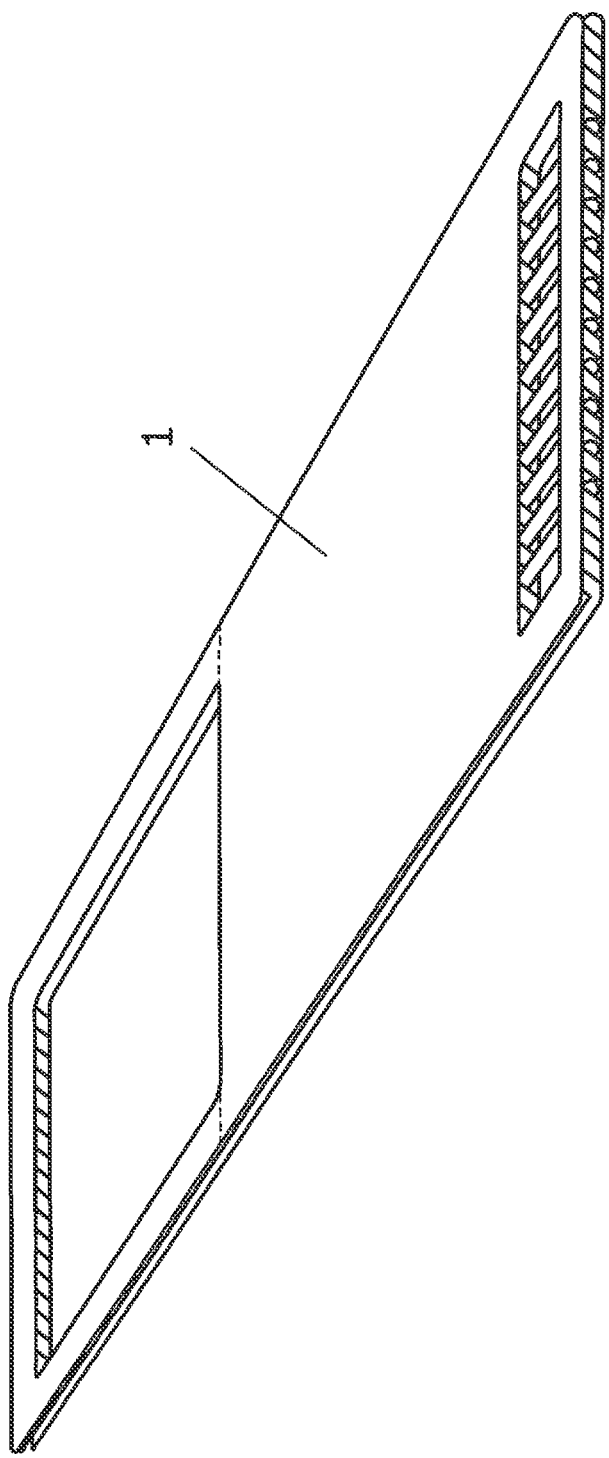
FIG. 2 is a diagram illustrating the side view of the radioactive needle holder.

FIG. 2. shows an exemplary side view of the needle package 1. This view will demonstrate the size of the needle package 1. The needle package 1 will try to use at most the minimal amount of construction material as possible. The needle package 1 contains a head 9 and bottom 10. The needle package 1 is not bent.

Figure 3:
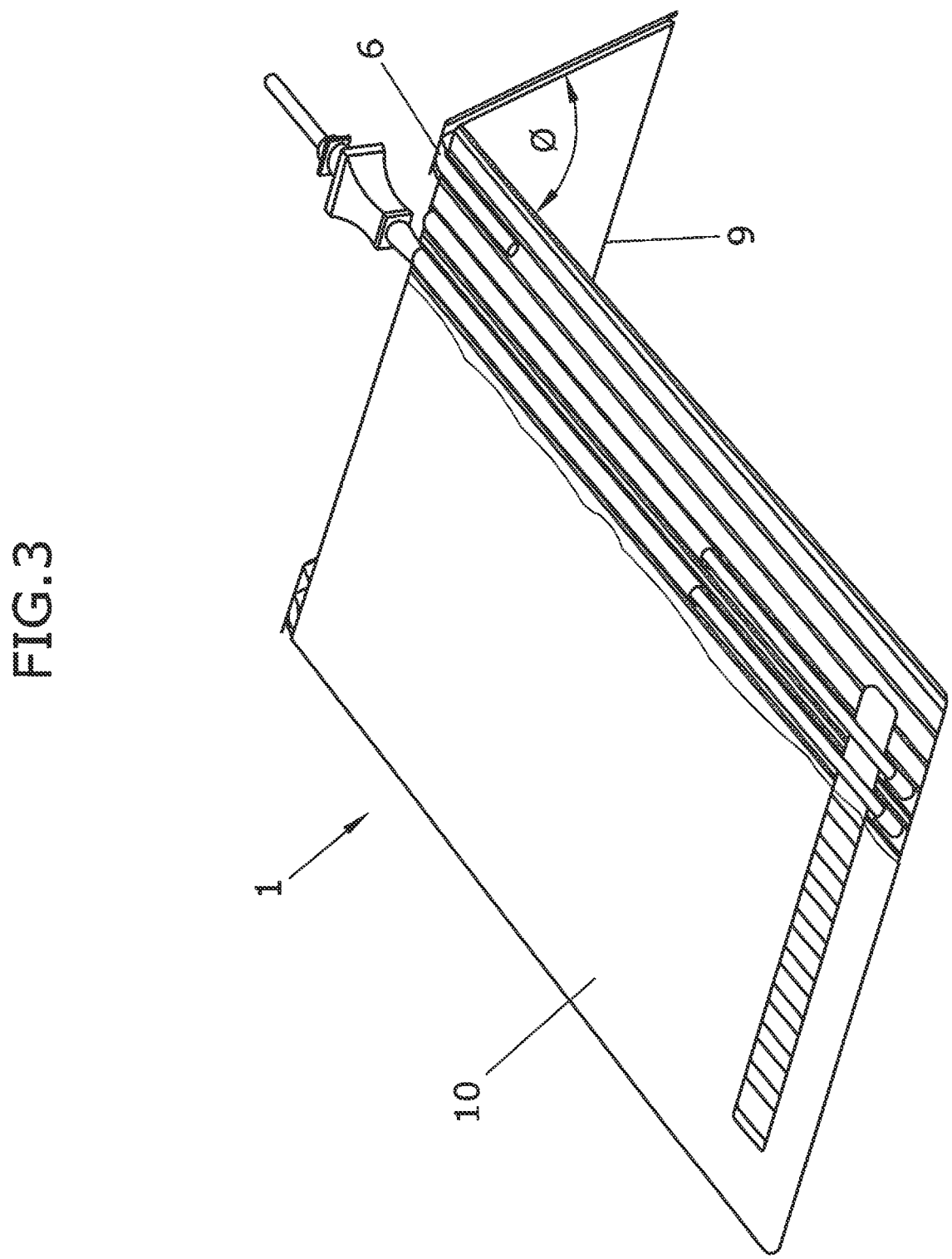
FIG. 3 is a diagram illustrating the side view of the needle holder with hinges to prop-up the needles.

FIG. 3. shows an exemplary side view of the needle package 1. This view will demonstrate that the head 9 may be bent to provide needle stand. The head 9 may be bent to any angle θ depending for the medical personnel's benefit. The needle package head is bent by the hinges 6. The hinges 6 may contain of any type of material that is flexible but sturdy. Therefore, this allows for quick access to the needle 2 for ease and comfort for medical personnel to remove the needles while providing treatment to the patient. By bending the needle package head 9, the needle package 1 provides a triangle shape stand. The medical personnel thereafter can place the stand anywhere.

The current procedure for shipping radioactive seeds is followed by the Supervisor receives paperwork package in a zip lock plastic bag. The supervisor checks paperwork corresponding a copy of order sheet. If necessary, enclose a copy of the invoice. After approval the paperwork package is sent to the packing area. Using the information on the paperwork, additional personnel check to see if the corresponding shipment is in the bin. Before packing, the Order is inspected for the contents of the bin to assure that all of the materials required for the order are present and correct. This inspection should include verification of: correct label information (including correct hospital name, patient identification, Isotope, quantity of seeds, activity, etc.); reviewed that all the trays, packages, containers of loose seeds present and properly labeled. Verify that there are no materials or paperwork in the bin that do not belong to the order, or match the requirements of the order. Record the results of this inspection on the radioactive material shipment-final checklist. Take a Conrugated Blue plastic box for shipments or Green box for shipments, depending on the type of radioactive material, from storage and place on metal cart. For strands in disk pack use corrugated blue plastic box for radioactive strands and corrugated Green Plastic box for different type of radioactive strands. For corrugated plastic trays for 10 needle trays or for 15 needle trays use a lead wrap to wrap up to three trays and place inside the blue box or green box for respectively using foam inserts for support. For shipments where the "Lead free" Demron® is used in place of the lead wrap, then cut the material to appropriate size so as to be able to wrap properly up to three trays or up to 20 single strand shipping tube pouches; For shipments made in the lead pouch Blue or Green place the tray containing the preloaded needles or pouches containing the loaded strands in tubes inside the pouch. The pouch can hold up to 3 thermoformed 15 up trays. For Strands in Disk Pack use a Lead Pouch for all radioactive seeds, placing one disk pack container in each pouch. Thereafter, print the labels for the shipment of packages. This process can be removed where shipment procedure requires that the trays be wrapped with lead or lead free material. By inserting the new, needle packages all the radiation should be blocked. The Radioactive Material Shipment-Final Checklist and order sheet should be filed with the extra copy of the Certificate and Bill of Lading.

The invention claimed is:

1. A needle package apparatus that comprises:
   a top portion and a bottom portion;
   a row of a plurality of needle slots equidistant apart that allows placement of a plurality of needles that contain radioactive seeds;
   a cylindrical coil that is inserted in the plurality of needle slots to hold said plurality of needles, wherein said cylindrical coil prevents leakage of radiation from the radioactive seeds;
   a set of hinges located at an end of said needle package, and disposed in an outer most of said plurality of needle slots and connecting between said top portion and said bottom portion; wherein the hinges can be bent to change an angle of said top portion with respect to said bottom portion by a medical personnel to create a stand; and
   a single end enclosure located at an end of said cylindrical coil to provide an enclosed cylinder.

2. A needle package apparatus of claim 1 wherein:
said cylindrical coil is composed of stainless steel, lead or demron wrap material, wherein the cylindrical coil diameter is not greater than 6 mm.

3. A needle package apparatus of claim 1 wherein:
said cylindrical coil is composed of a thickness of 1 mm to 3 mm, wherein the thickness depends upon an activity of the radioactive seeds.

4. A needle package apparatus of claim 1 wherein:
said cylindrical coil is fixed within said plurality of needle slots and covers said plurality of needles that contain radioactive seeds.

* * * * *